United States Patent
Hearn et al.

(10) Patent No.: US 9,980,520 B2
(45) Date of Patent: May 29, 2018

(54) INHALER HAVING A HEATER TO SELECTABLY VOLATILISE AT LEAST SOME COMPONENTS OF A COMPOSTION

(71) Applicant: Kind Consumer Limited, London (GB)

(72) Inventors: Alex Hearn, London (GB); Iain Mcderment, Hertfordshire (GB); Khine Zaw Nyein, Harrow (GB); David John Cottenden, Hertfordshire (GB)

(73) Assignee: KIND CONSUMER LIMITED, London (GB)

( * ) Notice: Subject to any disclaimer, the term of this patent is extended or adjusted under 35 U.S.C. 154(b) by 0 days. days.

(21) Appl. No.: 15/126,940

(22) PCT Filed: Mar. 19, 2015

(86) PCT No.: PCT/GB2015/050799
§ 371 (c)(1),
(2) Date: Sep. 16, 2016

(87) PCT Pub. No.: WO2015/140553
PCT Pub. Date: Sep. 24, 2015

(65) Prior Publication Data
US 2017/0105449 A1   Apr. 20, 2017

(30) Foreign Application Priority Data
Mar. 19, 2014   (GB) .................................. 1404940.7

(51) Int. Cl.
*A24F 13/00* (2006.01)
*A24F 47/00* (2006.01)
*B67D 7/02* (2010.01)

(52) U.S. Cl.
CPC .......... *A24F 47/008* (2013.01); *B67D 7/0294* (2013.01)

(58) Field of Classification Search
CPC ...... A24F 47/002; A24F 47/008; A24F 15/12; B67D 7/0294; B67D 7/0238
(Continued)

(56) References Cited

U.S. PATENT DOCUMENTS

| 4,393,884 A | 7/1983 | Jacobs |
| 4,907,606 A | 3/1990 | Lilja et al. |

(Continued)

FOREIGN PATENT DOCUMENTS

| CN | 202774134 U | 3/2013 |
| EP | 211003 A1 | 2/1987 |

(Continued)

OTHER PUBLICATIONS

International Search Report and Written Opinion dated Jun. 3, 2015 for Application No. PCT/GB2015/050799.
(Continued)

*Primary Examiner* — Hae Hyeon
(74) *Attorney, Agent, or Firm* — Patterson & Sheridan, L.L.P.

(57) ABSTRACT

An inhaler comprising a reservoir of an inhalable composition, a heater to selectably volatilize at least some components of the composition, and a power source arranged to selectively supply electrical power to the heater when the user inhales from the inhaler. The power source is arranged to heat the heater to a temperature that will volatilize some, but not all of the components of the composition.

19 Claims, 3 Drawing Sheets

(58) Field of Classification Search
USPC .......................................................... 131/329
See application file for complete search history.

(56) References Cited

U.S. PATENT DOCUMENTS

| | | | |
|---|---|---|---|
| 6,637,430 B1 | 10/2003 | Voges et al. | |
| 7,726,320 B2* | 6/2010 | Robinson | A24F 47/008 131/194 |
| 9,320,299 B2* | 4/2016 | Hearn | A24F 47/002 |
| 9,730,473 B2* | 8/2017 | Shinkawa | A24F 47/008 |
| 2011/0094523 A1 | 4/2011 | Thorens et al. | |
| 2011/0315152 A1 | 12/2011 | Hearn et al. | |
| 2012/0167906 A1 | 7/2012 | Gysland | |
| 2013/0037042 A1* | 2/2013 | Hearn | A24F 47/002 131/329 |
| 2013/0312739 A1 | 11/2013 | Rome et al. | |
| 2014/0000638 A1* | 1/2014 | Sebastian | A24F 47/008 131/328 |
| 2014/0034070 A1 | 2/2014 | Schennum | |
| 2014/0123989 A1* | 5/2014 | LaMothe | A24F 47/008 131/328 |
| 2015/0040925 A1* | 2/2015 | Saleem | A24F 47/008 131/328 |
| 2016/0095355 A1* | 4/2016 | Hearn | A24F 47/008 131/273 |
| 2016/0249680 A1* | 9/2016 | Liu | A24F 47/008 131/329 |
| 2016/0286851 A1* | 10/2016 | Hufnagel | A24B 15/30 |
| 2017/0086502 A1* | 3/2017 | Hearn | A24F 47/008 |
| 2017/0094999 A1* | 4/2017 | Hearn | A24F 47/008 |

FOREIGN PATENT DOCUMENTS

| | | |
|---|---|---|
| WO | 8604659 | 1/1986 |
| WO | 2014033437 A2 | 3/2014 |

OTHER PUBLICATIONS

United Kingdom Search Report for Application No. GB1404945.6 dated Sep. 8, 2014.

* cited by examiner

INHALER HAVING A HEATER TO SELECTABLY VOLATILISE AT LEAST SOME COMPONENTS OF A COMPOSTION

BACKGROUND OF THE INVENTION

Field of the Invention

The present invention relates to an inhaler.

Description of the Related Art

Conventional E-cigarettes have a volume of inhalable composition, a battery and a heating element to vaporise some of the composition as a user sucks on the end of the cigarette, the vaporised composition then being inhaled.

E-cigarettes are gaining increasing popularity as they provide an alternative to conventional smoking which eliminates the many carcinogens and toxic substances found in tobacco products.

E-cigarettes conventionally use an inhalable composition consisting of a high level of propylene glycol, glycerol, glycerin or glycol in which the nicotine (or alternative such as a flavouring) is solubilised. The high level of propylene glycol causes the composition to be viscous. This is beneficial as it can prevent unwanted evaporation of the composition out of the device and is usually contained in a cotton wadding, pad or other absorbent material. E-cigarettes generally comprise a heater or an ultrasonic atomiser which is in the vicinity of a small amount of the composition volume. Suction on the inlet end causes operation of the heater, and the substance in the vicinity of the heater is evaporated and inhaled. The relatively high viscosity of the composition ensures that the composition available to the heater is gradually replenished but generally prevents it from leaking from the absorbent material in the absence of heat.

While this is reasonably successful, there are two main drawbacks associated with electronic cigarettes. Firstly, the propylene glycol vaporises at a relatively high temperature such that this causes degradation of the composition generally used in E-cigarettes. This can lead to problems with dosage consistency and the presence of contaminants in the inhaled composition including the production of by-products such as formaldehyde, toluene and acrolein.

Secondly, the E-cigarettes require relatively high power to generate the high temperature. Moreover they normally require large batteries to deliver a total dose of vaporised composition to last the user the equivalent of between 20 to 40 cigarettes worth of inhalable composition. The cigarettes have the power to dispense at least one reservoir full of composition. As this large volume is dispensed at a high temperature, a large battery is required. Additionally since larger reservoirs and batteries are used, the nicotine dosage contained in E-cigarettes is high and potentially poses safety concerns when packaged in this format.

Broadly, such E-cigarettes can be divided into three categories, namely rechargeable, refillable and disposable. Those which are rechargeable come with a mains power adaptor. This is cumbersome for a user to carry around as it cannot readily fit into a pocket which is inconvenient. The relatively long recharge time is also inconvenient if a user only remembers that the charge has run down just before they go out.

There are also refillable E-cigarettes which require disassembly of the device and the replacement of the reservoir via a cartridge, liquid or absorbent material. However these are the subject of legal restrictions in many countries due to the availability of drug composition in unsealed containers. Moreover extra care is required in the process of replacing cartridges or material within the device, and extra effort is required by the user to refill which can be cumbersome and messy, especially if composition comes in contact with the skin.

A more recent development is a disposable cigarette. This is designed to last for a time equivalent to approximately 10-20 cigarettes, whereupon the cigarette and its container are thrown away. This is not environmentally friendly, particularly when the cigarette contains a relatively large battery and could be reused or recycled.

The present invention addresses some of the above problems.

SUMMARY OF THE INVENTION

According to the present invention there is provided an inhaler comprising a reservoir of an inhalable composition, a heater to selectably volatilise at least some components of the composition, and a power source arranged to selectively supply electrical power to the heater when the user inhales from the inhaler, the power source being arranged to heat the heater to a temperature that will volatilise some, but not all of the components of the composition.

Because the heater is configured to heat the composition to a temperature that will volatilise some, but not all, of the components of the composition, the temperatures required are less than those of the prior art. This reduces the power requirement of the inhaler and prevents the degradation of the inhaled formulation. Thus, preferably, the heater is arranged to heat the composition to between 40 and 180° C. and preferably 40° C. to 100° C. The ability to dispense at these temperatures is based on a recognition by the inventors that it is not necessary to volatilise all components of the formulation. Instead, the temperature is set at a level at which only certain components of the composition (such as ethanol) will volatilise while others (such as propylene glycol) will not.

Preferably the heater is arranged to heat the composition after it has left the reservoir. This avoids heating the composition in the reservoir itself thereby saving energy and reducing degradation of the composition.

Additionally or alternatively, other mechanisms may be employed to effect a fine aerosolisation of the non-volatilised formulation components. The reservoir may be pressurised for example, the composition may include a propellant, such as hydrofluoroalkane (HFA), to increase the pressure in the reservoir resulting in improved aerosolisation.

The inhaler may have any configuration but is preferably a simulated cigarette.

Additionally or alternatively there may be at least one airflow path arranged to draw air in through the side of the cigarette as a user inhales from an inhaling end, and impinge on the composition leaving the heater at the inhaling end. Such airflow will reduce the mean particle size of the plume. Preferably there is more than one such path, and preferably the paths are arranged to generate swirl around the main axis of the inhaler thereby generating further turbulence and causing greater reduction in particle size.

The airflow paths are preferably arranged to pass through a constriction in the vicinity of the outlet end of the inhaler thereby generating a Venturi effect and promoting suction of the composition out of the inhaler. The inhaler may be configured to have a throughflow of air from one end to the other when the user inhales from the outlet end. However, preferably, one or both of the effect of the propellant in the reservoir and the Venturi effect provided by the airflow paths provides the motive force to expel the composition from the reservoir.

The present invention also extends to a combination of an inhaler and a refill pack, the inhaler comprising a reservoir for an inhalable composition, a heater to selectively volatilise at least some components of the composition and at least one inhaler capacitor arranged to supply electrical power to the heater when a user inhales from the inhaler; the refill pack comprising a refill reservoir of inhalable composition and a battery coupled to a refill capacitor, and being arranged to engage with the inhaler and to refill the reservoir and recharge the inhaler capacitor from the refill capacitor, wherein the heater is configured to heat the composition to a temperature that will volatilise some, but not all of the components of the composition.

The inhaler of this combination may have any of the preferred features referred to above.

Preferably the pack is arranged to fully recharge and refill the inhaler from empty in less than 30 seconds and preferably less than 10 seconds.

The battery may be rechargeable, but is preferably non-rechargeable.

Preferably, the refill reservoir is pressurised with a propellant or a compressed gas, the inhaler reservoir having a closable refill valve and the refill pack having a complementary refill valve such that engagement of the inhaler with the pack will cause the two refill valves to open thereby allowing the pressurised composition to flow into the inhaler reservoir.

The refill pack is preferably configured such that it will automatically terminate the refill and recharge operations.

BRIEF DESCRIPTION OF THE DRAWINGS

An example of a combination of an inhaler and refill pack will now be described with reference to the accompanying drawings, in which.

DETAILED DESCRIPTION

The inhaler is in the form of a simulated cigarette having a generally cylindrical configuration the approximate size of a cigarette.

The inhaler has a cylindrical housing 1 which may be in one or more parts. The housing may be wrapped with a paper-like wrap to provide a more realistic cigarette-like appearance and feel.

Figure 1:
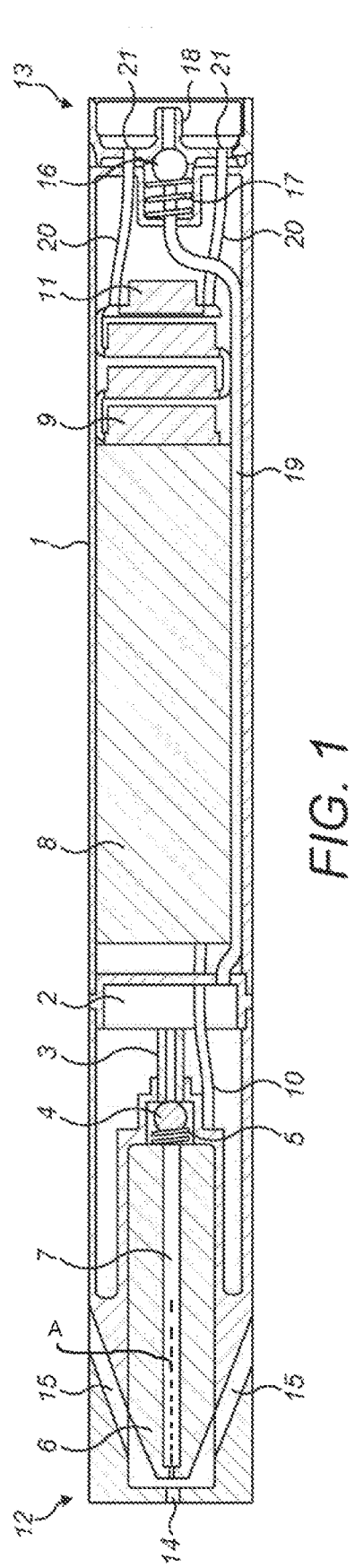
FIG. 1 is a schematic cross-section of an inhaler.

Within the housing 1 is a reservoir 2 of inhalable composition. The reservoir 2 has an outlet 3, flow from which is controlled by a ball valve 4 which is opened by an electromagnetic actuator against the action of a spring 5 which biases the ball valve 4 onto the outlet 3. As an alternative, the outlet valve may be a breath operated valve such as that disclosed in WO 2011/015825 and WO 2014/033438. Downstream of the ball valve 4 is a heater 6. This is made of any highly efficient conductive material, preferably fibreglass, and has an internal pathway 7 along its central axis for the passage of composition. The heater 6 is powered by a super capacitor 8 (also known as an ultra-capacitor). A suitable capacitor is sold by Maxwell Technologies as part of the HC series. This preferably has a capacity of 3-7 F and a diameter of 6 mm to 10 mm and a length of 5 to 50 mm. There may be more than one capacitor provided. FIG. 1 also shows an optional battery 9 which will charge the capacitor 8. However, the current preference is for no battery to be present. The capacitor 8 is connected to the heater 6 by a wire 10. Circuitry 11 is provided to control the operation of the inhaler.

The inhaler has an inhaling end 12 and a refill end 13. The inhaling end is provided with an outlet orifice 14 which is in communication with the internal pathway 7 from the heater. Surrounding the heater 6 in the vicinity of the inhaling end 12 are a number of air paths 15 as shown in FIG. 1. In practice, there may be a number of air paths arranged around the axis, but there are preferably 2 to 4 such passages. These are angled with respect to the main axis A of the inhaler as shown. They are also be offset with respect to the axis such they general swirl of the air about the main axis A. In particular, the air paths 15 are configured to generate a Venturi effect causing suction in the internal pathway 7 of the heater 6 when a user inhales from the inhaling end 12.

The refill end is provided with a refill valve 16 in the form of a ball valve which opens against the action of a spring 17 which biases the valve closed onto a refill nozzle 18. The refill valve 16 is connected to the reservoir 2 by a refill conduit 19 which extends past the capacitor 8 to provide fluid communication between the refill nozzle 18 and the reservoir 2. A pair of electrical contacts 20 with exposed ends 21 are arranged to provide an electrical connection from the refill end 13 to the opposite terminals of the capacitor 8.

When a user inhales from the inhaling end 12, air flow is detected by a sensor switch (not shown) in the air flow path 15 triggering the current flow from the capacitor 8 to the heater 6 in order to heat the composition. The composition comprises ethanol (boiling point 78.4° C.), nicotine (boiling point 247° C.), propylene glycol (boiling point 188° C.) and HFA (boiling point −26° C.). Thus, by heating the composition to a temperature of under 180° C., all but the nicotine and propylene glycolene are volatilised. Preferably the composition is heated to 80° C. which will comprise the ethanol but not the propylene glycol. The result of this heating is a mixture of non-volatilised liquid formation and vapour.

At the same time, the ball valve 4 is opened by the electromagnetic actuator. Thus, the composition in the reservoir 2, which may be pressurised to for example, 6 bar if a propellant is used, leaves the reservoir along the internal pathway 7 assisted by the suction force generated by the airflow in the air paths 15. This airflow also serves to break up the composition ensuring that the plume emitted from the outlet orifice 4 has a fine aerosolisation that promotes higher pulmonary deposition.

The refill pack will now be described by reference to FIG. 2. This shows the inhaler of FIG. 1 inserted into the refill pack with the refill end 13 lowermost. The refill pack is approximately the size and shape of a standard cigarette pack but can have any configuration.

The refill pack comprises a housing 30 and is broadly divided into three sections namely, from left to right (in FIG. 2), a storage port 31 to receive the inhaler, a power supply 32 and a composition refill reservoir 33. These are connected across the base of the housing 30 as described below.

Figure 3:
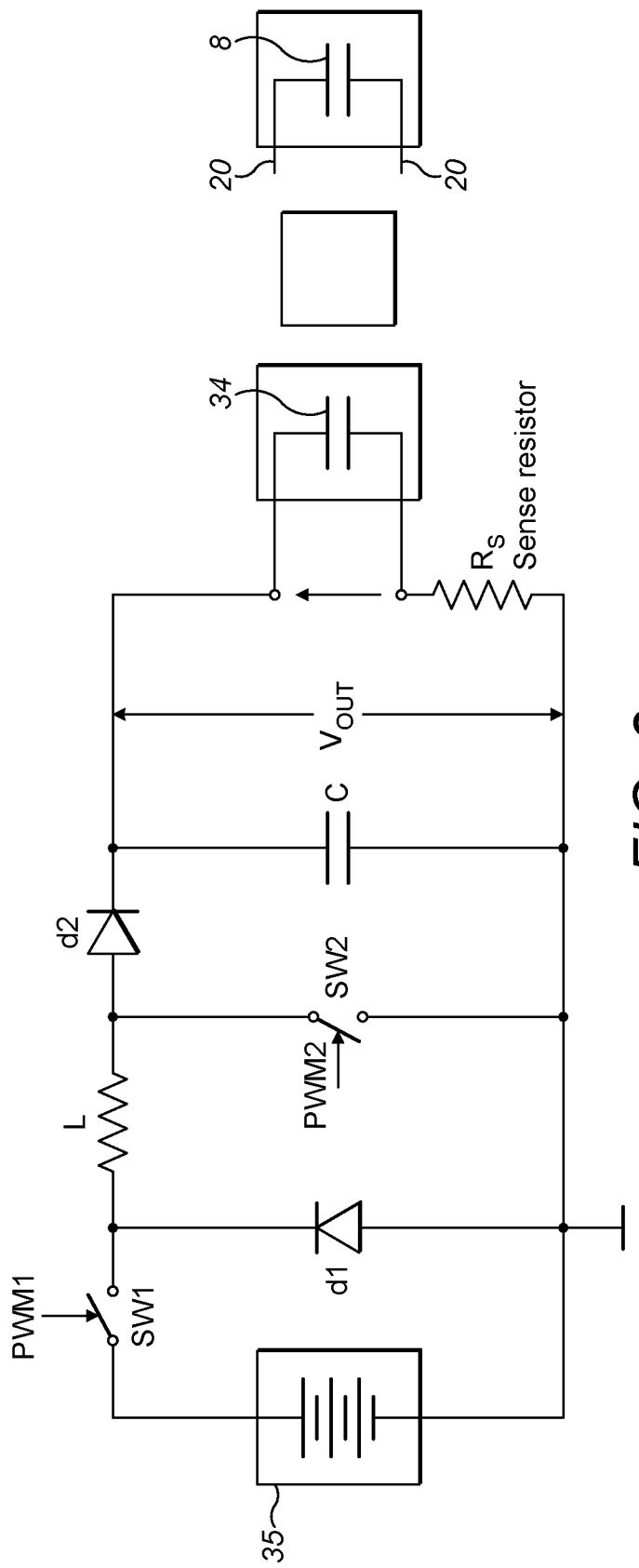
FIG. 3 is a circuit diagram for the recharging operation.

The power supply 32 comprises a capacitor 34 which is charged from the battery 35 as shown in FIG. 3. Control circuitry 36 is retained in place by a screw cap 37. The composition refill reservoir 33 is pressurised by a plunger 38 which is biased downwardly by a spring 39 held in place by a screw cap 40. The bottom end of the reservoir is connected by a refill duct 41 to a refill valve 42 beneath the storage port 31.

The refill valve 42 is a ball valve which is biased closed by a spring and which is opened, in use, by the refill nozzle 18 of the inhaler which presses downwardly on the refill valve 42.

A release spring 43 is provided in the housing 30 underneath the storage port 31. This spring will push the inhaler away from the refilling position to a storage position when the refilling process is complete. This may be done, for example, by releasing the inhaler when a certain priority is detected which indicates that the refill operation is complete.

Figure 2:
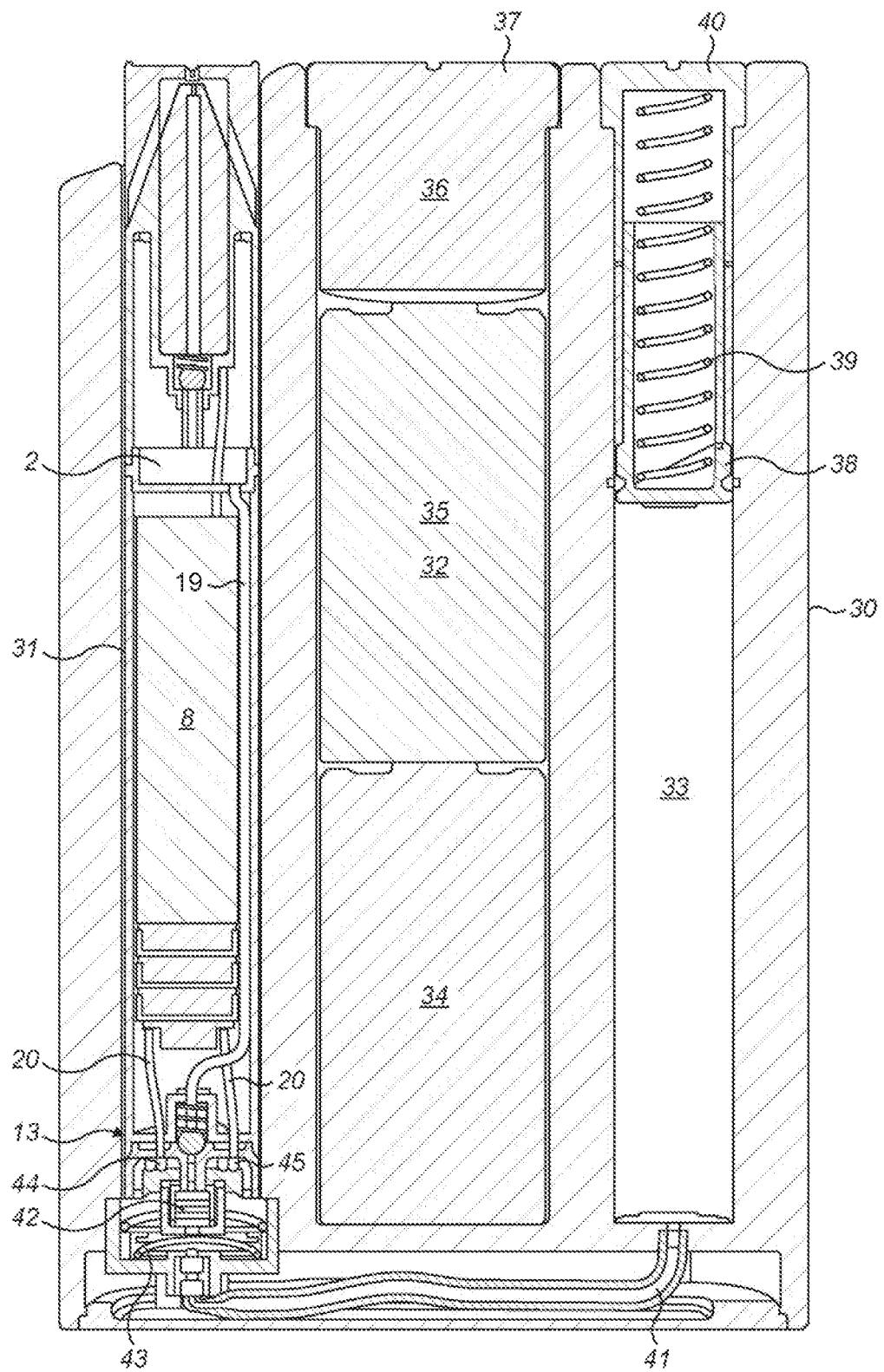
FIG. 2 is a schematic cross-section of an inhaler within a refill pack.

When the reservoir 2 is depleted of composition, the inhaler is inserted into the housing 30 in the orientation as shown in FIG. 2 and downward pressure is applied to overcome the release spring 42. The refill nozzle 18 opens the refill valve 42 such that the pressure in the composition refill reservoir 33 is sufficient to lift the refill valve 16 in the inhaler thereby allowing composition to flow along the refill conduit 19 and link to the reservoir 2. The refill operation is automatically terminated as described above and the release spring urges the inhaler to the storage position.

At the same time as the inhaler is being refilled, the exposed ends 21 of the electrical contacts 20 make contact with inner 44 and outer 45 charging plate rings in the housing 30 which are electrically coupled to the capacitor 34. This causes the inhaler capacitor 8 to be recharged simultaneously with the refill. The recharge circuit is shown in FIG. 3.

The invention claimed is:

1. An inhaler comprising a pressurized reservoir of an inhalable composition, a heater to selectably volatilise at least some components of the composition, and a power source arranged to selectively supply electrical power to the heater when the user inhales from the inhaler, the power source being arranged to heat the heater to a temperature that will volatilise some, but not all of the components of the composition.

2. The inhaler according to claim 1, wherein the heater is arranged to heat the composition to between 40 and 180° C.

3. The inhaler according to claim 2, wherein the heater is arranged to heat the composition to between 40 and 100° C.

4. The inhaler according to claim 1, wherein the composition includes ethanol and the heater is arranged to heat the formulation to volatilise the majority of the ethanol.

5. The inhaler according to claim 1, wherein the composition includes propylene glycol and the heater is arranged to heat the formulation not to volatilise the majority of the propylene glycol.

6. The inhaler according to claim 1, wherein the heater is arranged to heat the composition after the composition has left the reservoir.

7. The inhaler according to claim 1, further comprising at least one airflow path arranged to draw air in through the side of the inhaler as a user inhales from an inhaling end, and impinge on the composition leaving the heater at the inhaling end.

8. The inhaler according to claim 7, further comprising more than one airflow path and wherein the more than one airflow paths are arranged to generate swirl around a main axis of the inhaler.

9. The inhaler according to claim 1, wherein the inhaler is a simulated cigarette.

10. The inhaler according to claim 1, wherein the composition includes a propellant.

11. The inhaler according to claim 10, wherein the propellant is HFA.

12. A combination of an inhaler and a refill pack, the combination comprising:
the inhaler comprising a reservoir for an inhalable composition, a heater to selectively volatilise at least some components of the composition and at least one inhaler capacitor arranged to supply electrical power to the heater when a user inhales from the inhaler; and
the refill pack comprising a refill reservoir of inhalable composition and a battery coupled to a refill capacitor, and being arranged to engage with the inhaler and to refill the reservoir from the refill reservoir and recharge the inhaler capacitor from the refill capacitor, wherein the heater is configured to heat the composition to a temperature that will volatilise some, but not all of the components of the composition.

13. The combination according to claim 12, wherein the heater is arranged to heat the composition to between 40 and 180° C.

14. The combination according to claim 13, wherein the heater is arranged to heat the composition to between 40 and 100° C.

15. The combination according to claim 12, wherein the refill pack is arranged to fully recharge and refill the inhaler from empty in less than 30 seconds and preferably less than 10 seconds.

16. The combination according to claim 12, wherein the battery is non-rechargeable.

17. The combination according to claim 12, wherein the refill reservoir is pressurised with a propellant or a compressed gas, the inhaler reservoir having a closable refill valve and the refill pack having a complementary refill valve such that engagement of the inhaler with the refill pack will cause the two refill valves to open thereby allowing the pressurised composition to flow into the inhaler reservoir.

18. The combination according to claim 12, wherein the refill pack is configured such that the refill pack will automatically terminate the refill and recharge operations.

19. An inhaler comprising a pressurized reservoir of an inhalable composition, a heater to selectably volatilise at least some components of the composition, and a power source arranged to selectively supply electrical power to the heater when the user inhales from the inhaler, the power source being arranged to heat the heater to a temperature that will volatilise some, but not all of the components of the composition, further comprising at least one airflow path arranged to draw air in through the side of the inhaler as a user inhales from an inhaling end, and impinge on the composition leaving the heater at the inhaling end, wherein the inhaler further comprising more than one airflow path and wherein the airflow paths are arranged to pass through a constriction in the vicinity of an outlet end of the inhaler thereby generating a venturi effect and promoting suction of the composition out of the inhaler.

* * * * *